United States Patent [19]

Golyakhovsky et al.

[11] Patent Number: 4,800,879
[45] Date of Patent: Jan. 31, 1989

[54] DISPOSABLE VASCULAR OCCLUDER

[76] Inventors: Vladimir Golyakhovsky, 165 W. 91st St., New York, N.Y. 10024; Robert Lerner, 315 E. 65th St., New York, N.Y. 13021

[21] Appl. No.: 71,406
[22] Filed: Jul. 9, 1987
[51] Int. Cl.⁴ .............................................. A61B 17/12
[52] U.S. Cl. .................... 128/325; 128/346
[58] Field of Search ....... 128/346, 325, 326, DIG. 25; 251/9, 10

[56] References Cited

U.S. PATENT DOCUMENTS

| D. 190,787 | 6/1961 | Schneider | D83/12 |
|---|---|---|---|
| 3,061,263 | 10/1962 | Butler | 251/9 |
| 3,106,919 | 10/1963 | Churchville | 128/346 |
| 3,247,852 | 4/1966 | Schneider | 128/346 |
| 3,538,917 | 11/1970 | Selker | 128/326 |
| 3,675,656 | 7/1972 | Hakim | 128/325 |
| 3,730,186 | 5/1973 | Edmunds | 128/325 |
| 3,831,583 | 8/1974 | Edmunds, Jr. et al. | 128/1 R |
| 3,833,003 | 9/1974 | Taricco | 128/347 |
| 4,112,944 | 9/1978 | Williams | 128/346 |
| 4,188,953 | 2/1980 | Klieman | 128/325 |
| 4,227,730 | 10/1980 | Alexander et al. | 294/16 |
| 4,256,094 | 3/1981 | Kapp | 128/325 |
| 4,390,019 | 6/1983 | Le Veen | 128/346 |
| 4,404,971 | 9/1983 | Le Veen et al. | 128/348.1 |
| 4,478,219 | 10/1984 | Rozario et al. | 128/325 |
| 4,531,519 | 7/1985 | Dunn et al. | 128/327 |
| 4,542,743 | 9/1985 | Dunn et al. | 128/327 |
| 4,545,377 | 10/1985 | Cerwin | 128/325 |
| 4,586,501 | 5/1986 | Claracq | 128/325 |

FOREIGN PATENT DOCUMENTS 2177748  1/1987  United Kingdom ............... 128/325

Primary Examiner—Andrew M. Dolinar
Attorney, Agent, or Firm—Henry R. Lerner

[57] ABSTRACT

A disposable vascular occluding device for temporarily stopping or interrupting blood flow in veins or arteries of the body during vascular surgery and emergency trauma surgery is constructed with two plastic arms connected at one end by a hinge for pivoting the arms towards and away from each other and connected at an end opposite the hinged end by a toothed latch for releasably securing the plastic arms in a closed position with inner surfaces thereof confronting each other. The inner surfaces of the plastics arms have semi-circular cavities formed therein which are shaped to conform to the blood vessel to be occluded. The inner surfaces of the plastic arms are lined by a pair of partially-inflated soft plastic balloons, centered in the cavities, one of which is further inflatable by means of an ordinary syringe through a valve in one of the plastic arms. The device facilitates occlusion of a blood vessel with minimal or no traumatization of the wall of the blood vessel.

8 Claims, 4 Drawing Sheets

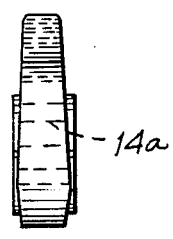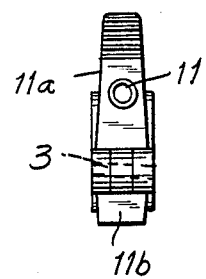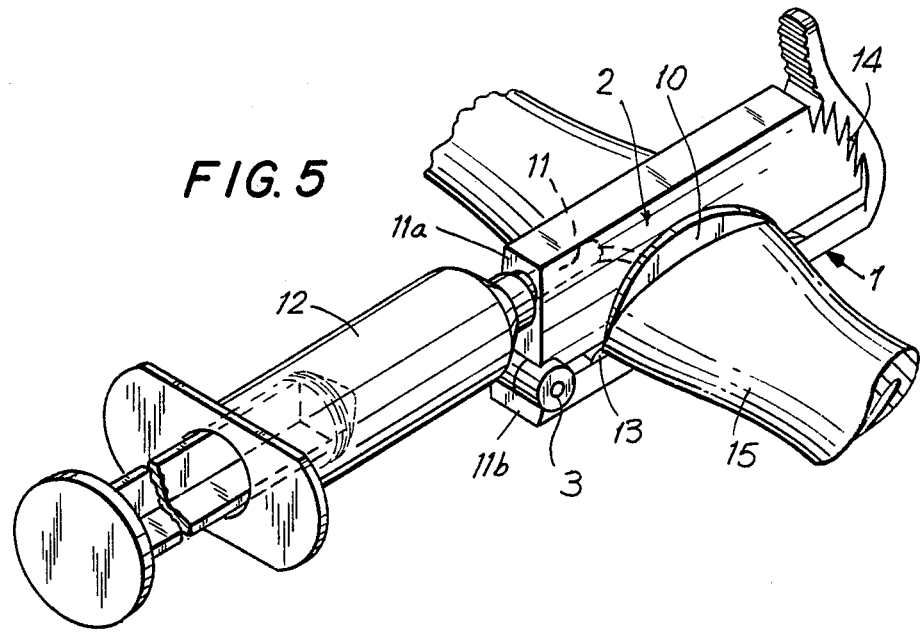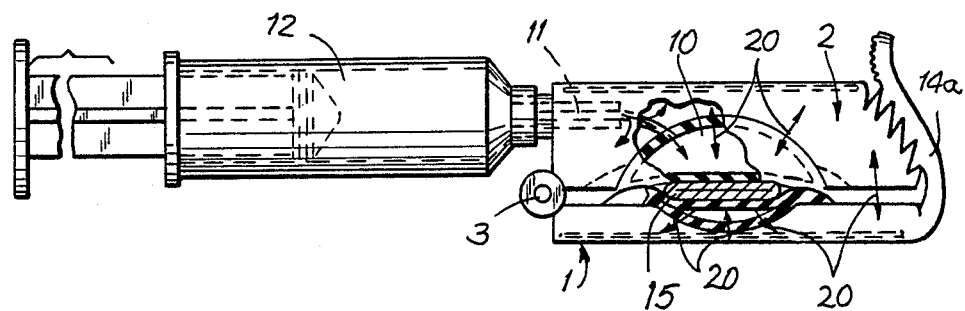

DISPOSABLE VASCULAR OCCLUDER

BACKGROUND OF THE INVENTION

The present invention relates to a vascular occluding device for use in vascular surgical procedures that allows for simplicity of application and produces minimum trauma to the vessel that is occluded.

Vascular surgery is a burgeoning medical specialty usually required temporary vascular occlusion of arteries and veins of different sizes and locations in the body. Conventional methods of securing such occlusions when needed have involved the use of a variety of vascular occluding devices.

Several types of metal occlusion clamps are known and used in the field, such as those known as the bulldog, serrefine, rubber-shod, Satinsky and Fogarty clamps. Various forms of tourniquets are also employed. Dual-armed occluding clips are known, such as those disclosed in U.S. Pat. Nos. 3,061,263, 3,247,852, 4,227,730 and U.S. Pat. No. De.190,787. Similarly, U.S. Pat. No. 4,478,219 discloses hinged plastic tubes for occluding a vessel. Tapes which can encircle a blood vessel and then be externally tightened have also been proposed, such as in U.S. Pat. No. 3,880,166.

Inflatable balloons have been suggested in a number of instances for use in occluding devices. For example, as disclosed in U.S. Pat. Nos. 3,833,003 and 4,404,971 it has been proposed to insert an inflatable balloon inside a blood vessel and then inflate the balloon to temporarily occlude blood flow.

Conversely, various proposals have been made to occlude blood vessels utilizing a balloon device applied externally to the blood vessel. For instance, as set forth in U.S. Pat. No. 3,538,917, an occlusion clip includes a preferably round support member and an inflatable balloon within the support member for occluding a vessel. U.S. Pat. No. 3,675,656 suggests an occluding device employing a support member having therein a bottom channelled jaw and an upper inflatable chamber. A blood vessel is occluded by situating the blood vessel between the balloon and jaw and inflating the balloon, thereby pressing the blood vessel against the channelled jaw. U.S. Pat. Nos. 3,730,186 and 3,831,583 suggest a device similar to that of U.S. Pat. No. 3,538,917 which may be permanently implanted in the body. U.S. Pat. Nos. 4,531,519 and 4,542,743 disclose a flexible support member with an inflatable chamber for wrapping around a blood vessel, followed by inflation and occlusion. Finally, In Vivo Metric Systems (IVM) markets a number of blood vessel occluders, including an occluding clip having a hook shape, the base end of the hook having an inflatable diaphragm for occluding the vessel between the diaphragm and hook.

Despite the plethora of vascular occluders presently available, each of which has its place in vascular surgery, many are cumbersome and expensive to manufacture and all result in more or less damage to the vessel wall, especially the inner lining (the intima) of the vessel. This trauma often leads to failure or other serious consequence of vascular surgery.

Accordingly, the need still exists for a vascular occluding device which is effective, easy to apply to any vessel in any body location and which minimizes trauma to the blood vessel during application.

SUMMARY OF THE INVENTION

An object of the present invention is to provide a vascular occluding device which minimizes or eliminates trauma to blood vessels during temporary occlusion of arteries and veins during vascular surgery.

A further object of the present invention is to provide a vascular occluding device which is disposable, inexpensive to manufacture, readily available, easy to apply and which can be manufactured in various sizes so that a device can be available for any size blood vessel at any body location.

Yet another object of the present invention is to provide a vascular occluding device which can easily accommodate special anatomical situations and fit around various blood vessels better than existing occluding devices.

These and other objects are achieved, in accordance with the present invention, by a vascular occluding device, usually made of plastic, comprising upper and lower arm connected at first ends thereof by pivoting means for moving the upper and lower arms towards and away from each other between closed and open positions thereof and releasably connected at second ends thereof by means, preferably a toothed latch, for releasably securing the arms together in a closed position. Inner surfaces of the upper and lower arms confront ecah other and contain cavities therein shaped to conform to a desired blood vessel. Partially-inflated soft balloons line the inner surfaces of the upper and lower arms and are centered in the cavities. The balloon lining the inner surface of the upper arm is inflatable beyond its original partially-inflated state through a valve, preferably a one-way valve, in the upper arm by means, for example, of an ordinary syringe. Accordingly, the occluder device can be inserted around a blood vessel in the open position and closed by engaging the toothed latch to secure and occlude a blood vessel between the balloons by soft pressure with minimum trauma to the calcified wall of the blood vessel.

In accordance with a further aspect of the invention, the lower arm is significantly thinner than the upper arm to facilitate insertion around a blood vessel. In an alternative embodiment, the upper and lower arms are specially shaped to further facilitate placement around the vessel.

BRIEF DESCRIPTION OF THE DRAWINGS

The present invention will be better understood by reference to the accompanying drawings, in which:

FIG. 4a is an end view of the latched end of the vascular occluder shown in FIG. 1;

FIG. 4b is an end view of the hinged end of the vascular occluder shown in FIG. 1;

FIG. 5 is a side perspective view of the vascular occluder of FIG. 1 with an inflating syringe in operative engagement therewith;

FIG. 6 is a side elevation view of the vascular occluder shown in FIG. 5 illustrating the pressure applied to an occluded blood vessel;

DETAILED DESCRIPTION OF THE PREFERRED EMBODIMENTS

Figure 3A:
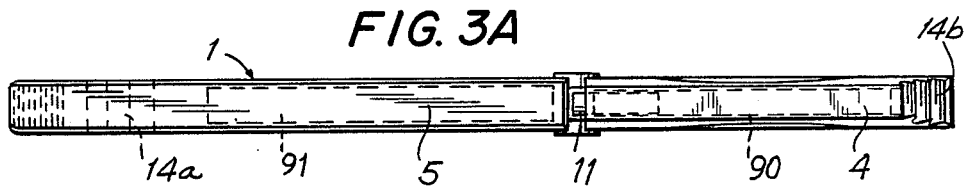
FIG. 3a is a top plan view of the device of FIG. 3.
Figure 3:
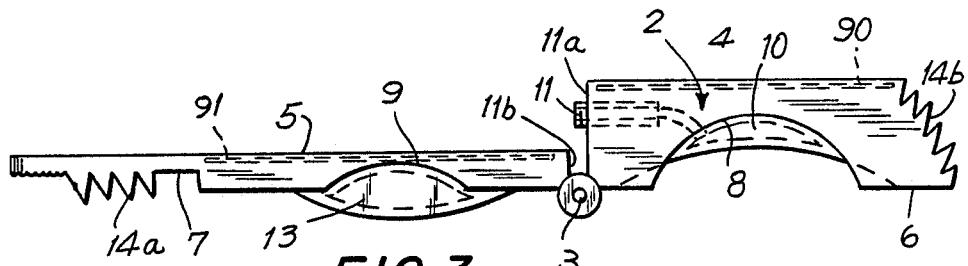
FIG. 3 is an elevation side view of the vascular occluder shown in FIG. 2 in an open position.
Figure 7:
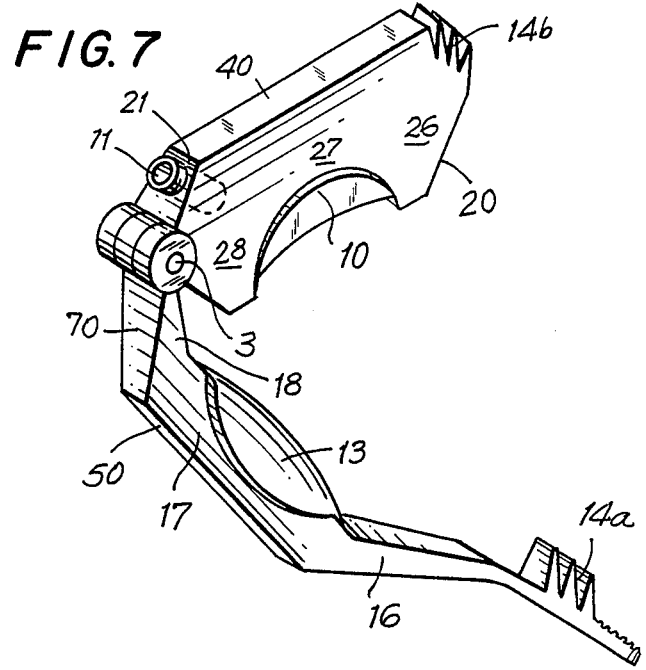
FIG. 7 is a side perspective view of a second embodiment of the disposable vascular occluder device in accordance with the invention in a partially open position.
Figure 8:
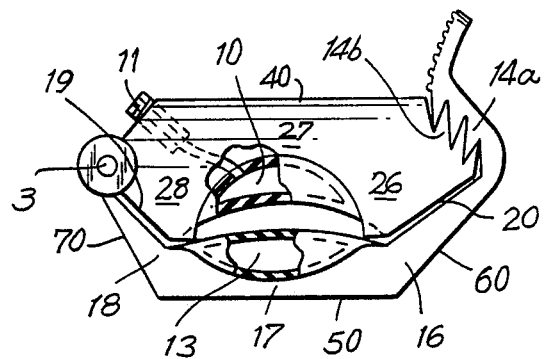
FIG. 8 is a side elevation view of the vascular occluder of FIG. 7 in a closed position.
Figure 9:
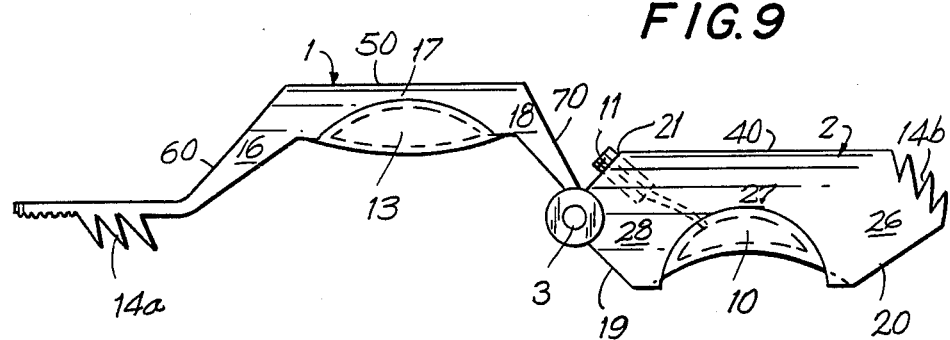
FIG. 9 is a side elevation view of the vascular occluder of FIG. 8 in a fully open position.
Figure 10:
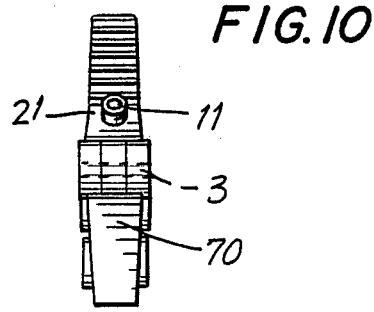
FIG. 10 is an end view illustrating the hinged ends of the vascular occluder of FIG. 8.

As shown in FIGS. 1 to 7, a first embodiment of the vascular occluder device in accordance with the invention, generally denoted as A, comprises two arms 1 and 2, preferably made of plastic, connected at end side surfaces 11a and 11b thereof by a hinge 3. Hinge 3 permits relative pivotal movement of arms 1 and 2 towards and away from each other to close and open the device. When view from the top, upper arm 2 has an outer top surface 4 shaped as a rectangle, as can be seen in FIG. 3. Similarly, when viewed from the bottom, lower arm 1 has an outer bottom surface 5 also shaped as a rectangle, as can also be ssen in FIG. 3a. As can be seen especially in FIGS. 1 to 3, outer surfaces 4 and 5 have planar edges.

Arms 1 and 2 are also constructed with inner surfaces 6 and 7 which confront each other when the device A is closed. Inner surfces 6 and 7 contain indentations defining cavities 8 and 9 therein. Cavities 8 and 9 are formed in the shape of a blood vessel to be occluded. It is preferred that cavities 8 and 9 take a semicircular configuration, as in the FIG. 1–7 embodiment.

The inner surfce 6 of upper arm 2 is lined with a soft plastic partially-inflated wedge-shaped balloon 10 centered in the cavity 8. While balloon 10 in its original condition is provided as partially-inflated, it is possible to further inflate balloon 10. For this purpose, a one-way valve 11 located at the hinged end of the device A on side surface 11a of upper arm 2 communicates between the outside atmosphere and balloon 10. Accordingly, balloon 10 can be gradually further inflated beyond its original state through valve 11 by insertion of, for example, an ordinary disposable syringe 12, shown in FIGS. 5 and 6.

It is within the scope of the present invention that valve 11 comprise a two-way valve, so that balloon 10 can be inflated or deflated as necessary to achieve the desired degree of inflation for any particular surgical situation.

The inner surface 7 of lower arm 1 is lined with a soft plastic partially-inflated wedge-shaped balloon 13 centered in the cavity 9. Balloon 13, in contrast to balloon 10, is provided as permanently partially-inflated to any desired degree of inflation, and the device A is not constructed with any means for further inflating balloon 13.

Lower arm 1 is significantly thinner and narrower than upper arm 2. The relative thinness and narrowness of lower arm 1 facilitates easy encirclement of the vessel to be occluded without damaging the calcified blood vessel walls and with minimal dissection, disturbance, or displacement of adjacent body structures during placement and use of the occluder. As an example, the thickness of lower arm 1 is preferably 3 to 4 mm for small diameter vessels, about 1 cm for larger diameter vessels and 2.5 to 3 cm for the aorta.

A closure mechanism 14 for releasably maintaining arms 1 and 2 in a closed position is integrally formed at the end of device A opposite hinge 3. Mechanism 14 is constructed of interlocking toothed latch 14a and flexible, resilient toothed latch 14b formed, respectively, on the ends of arms 1 and 2. Toothed latches 14a and 14b each have a plurality of teeth and thus can be interlocked at several different incremental settings. The number and location of teeth may be varied as desired.

When the vascular occluder device is closed around a vein or artery, the toothed latch 14 is closed to hold the device in the closed position with balloons 10 and 13 directly contacting, encircling and compressing vessel 15 so that the vessel is only minimally traumatized, if at all. Toothed latch 14 facilitates occlusion of a blood vessel in an atraumatic fashion, with either minimal compression, moderate compression, or maximum compression rigidly maintained, depending on the number of teeth engaged. The solid arrows 20 in FIG. 6 illustrate the pressure distribution around vessel 15 as the vessel is occluded between balloons 10 and 13. Semicircular cavities 8 and 9 facilitate adaptation of the device to the vessel encircled. Moreover, partially-inflated balloon 10 can be further inflated through valve 11, to any degree, depending on the pressure required to arrest blood flow in the vessel. On occasion, the initial pressure of the partially-inflated balloons 10 and 13 and the engagement of latch 14 is sufficient to stop blood flow without further inflation of balloon 10 through valve 11.

Figure 1:
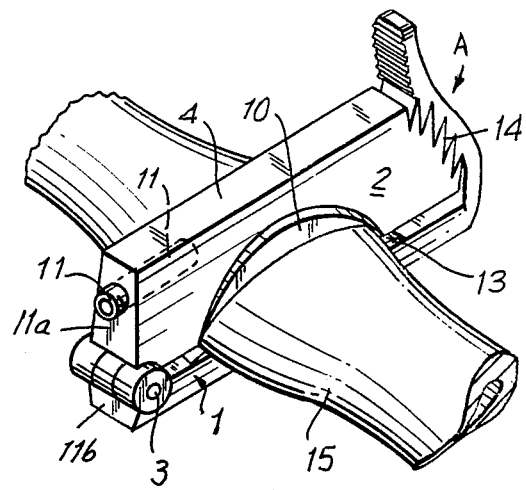
FIG. 1 is a side perspective view of a first embodiment of a disposable vascular occluder device in accordance with the invention in a closed position surrounding and occluding a blood vessel.
Figure 2:
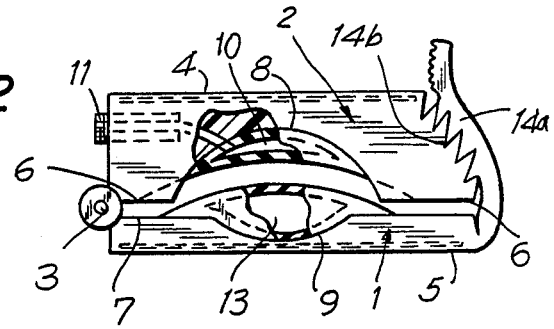
FIG. 2 is an elevation side view of the vascular occluder of FIG. 1 in a closed position without the blood vessel.

FIGS. 1, 5 and 6 illustrate the first embodiment of the vascular occluder device of the present invention closed around a blood vessel 15 with maximum compression applied by toothed latch 14. Balloon 10 is gradually inflated by syringe 12 through valve 11 to the requisite pressure after closure of the device A around vessel 15. Provision of the balloons 10 and 13 insures that any pressure exerted on blood vessel 15 is uniformly distributed and that the occlusion occurs with the minimum amount of force necessary, as shown by the solid arrows 20 in FIG. 6.

FIGS. 7 to 10 illustrate a second embodiment of the vascular occluder device in accordance with the invention, wherein like numerals refer to the same elements as in the first embodiment. In this alternative embodiment, arms 1 and 2 are shaped to further facilitate placement of the device around a blood vessel. Thus, lower arm 1 is composed of three sections 16, 17 and 18. The bottom outer surface of lower arm 1 is multi-faceted and constructed with a central planar surface 50 and a pair of opposed side surfaces 60 and 70 extending in diverging angular relation from opposite ends of central planar surface 50, which is preferably rectangular.

Similarly, upper arm 2 is composed of three sections 26, 27 and 28. The inner surface of upper arm 2 is constructed with a pair of side surfaces 19 and 20 extending in diverging angular relation from opposite ends of cavity 8 to, respectively, hinge 3 and toothed latch 14b. Hinge 3 is located nearer the top surface of upper arm 2 than in the first embodiment, as can be seen by comparing FIGS. 4b and 10, and valve 11 is located at an angle on the upper arm 2 on a side surface 21 thereof. Top outer surface 40 of upper arm 2 is a planar rectangular surface.

This overall construction, namely, the shape of arms 1 and 2, which impart a hexagonal profile to the device, renders the same more compact and easier to insert and close around a blood vessel, even in confined anatomical situations and locations.

In a preferred aspect of the present invention, the plastic arms 1 and 2 have incorporated therein rectangular radio-opaque strips 90 and 91, as can be seen in FIGS. 3 and 3a. Accordingly, during use, visualization and location of the device is possible by taking X-rays, which facilitates the surgery.

Thus it can be seen that the vascular occluder device as aforedescribed can be used to temporarily stop or interrupt arterial or venous blood flow in an improved manner during vascular surgical procedures performed on human patients or in experimental animal procedures. The device is useful in emergency, trauma surgery, in nearly every case of elective vascular surgery and in the animal research laboratory. Moreover, since the device preferably consists almost or entirely of plastic parts, it can be manufactured very economically and is disposable after a single usage, thus eliminating cumbersome sterilization techniques for used medical devices.

Figure 11:
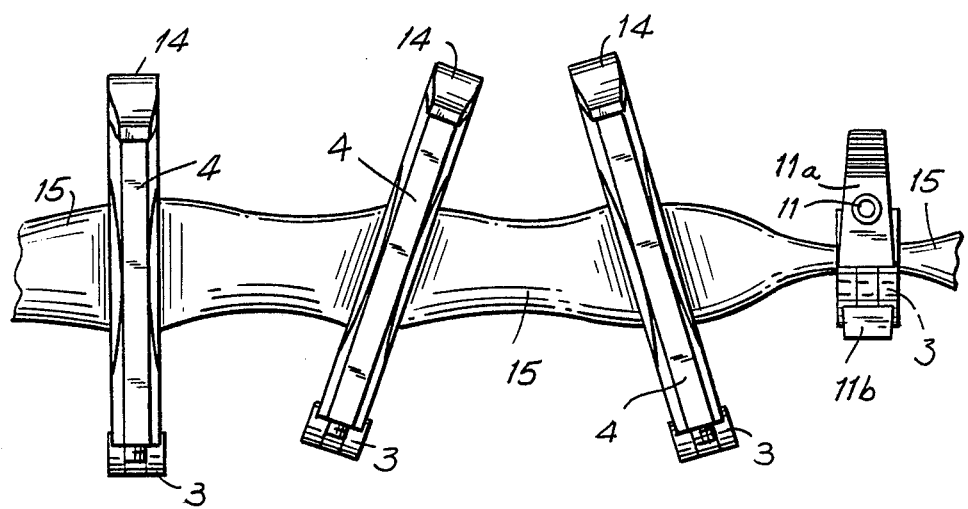
FIG. 11 is a schematic view of a pluralityi of the vascular occluders of FIG. 1 closed around a blood vessel at varying angles.

Additionally, the device can be manufactured in a variety of desired sizes, thus rendering the device applicable to virtually every blood vessel in the body. Also, the device can readily and freely be placed around a vessel in vertical, horizontal, oblique, or inclined directions, as illustrated generally in FIG. 11, thus enhancing any necessary modifications required by the involved surgical procedure or size and depth of a surgical wound. Accordingly, the invention provides an inexpensive, disposable, atraumatic vascular occluder which minimizes or eliminates rupture of the calcified wall of blood vessels, thus eliminating prior art surgery complications in the use of such devices.

It will be understood that the specification and preferred embodiments are illustrative but not limitative of the present invention. Other embodiments within the spirit and scope of the invention will suggest themselves to those skilled in the art.

What we claim is:

1. A disposable vascular occluder device for temporarily stopping or interrupting arterial or venous blood flow in an artery or vein during surgical procedures, comprising,
   (a) a first arm having an outer surface and an inner surface, said inner surface having a cavity therein;
   (b) a second arm having an outer surface and an inner surface, said inner surface having a cavity therein;
   (c) partially-inflated balloon means provided in said first and second arm cavities;
   (d) means pivotally connecting said first and second arms at first ends thereof, to permit said arms to be pivoted towards each other to assume a closed condition in which the inner surfaces thereof are in confronting relation, and pivoted away from each other to assume an open condition;
   (e) means for releasably maintaining said arms in said closed condition, in which said inner surfaces are in said confronting relation;
   (f) whereby said arms, when in said open condition thereof, can be inserted around a blood vessel and can thereafter be pivoted to said closed condition thereof, wherein said blood vessel is occluded between said balloon means under soft pressure with minimized trauma to the blood vessel;
   (g) said balloon means comprising a first partially-inflated balloon provided in said first arm cavity and a second partially-inflated balloon provided in said second arm cavity; and
   (h) means for controllably inflating said first partially-inflated balloon beyond said partially-inflated state to adjust the pressure of said balloon means on said blood vessel;
   (i) said controlled inflation means comprising a one-way valve in said first arm communicating with said first balloon, whereby said first balloon can be controllably inflated by a syringe inserted into said valve.

2. A new disposable vascular occluder device for temporarily stopping or interrupting arterial or venous blood flow in an artery or vein during surgical procedures, comprising,
   (a) a first arm having an outer surface and an inner surface, said inner surface having a cavity therein;
   (b) a second arm having an outer surface and an inner surface, said inner surface having a cavity therein;
   (c) partially-inflated balloon means provided in said first and second arm cavities;
   (d) means pivotally connecting said first and second arms at first ends thereof, to permit said arms to be pivoted towards each other to assume a closed condition in which the inner surfaces thereof are in confronting relation, and pivoted away from each other to assume an open condition;
   (e) means for releaseably maintaining said arms in said closed condition, in which said inner surfaces are in said confronting relation;
   (f) whereby said arms, when in said open condition thereof, can be inserted around a blood vessel and can thereafter be pivoted to said closed condition thereof, wherein said blood vessel is occluded between said balloon means under soft pressure with minimized trauma to the blood vessel;
   (g) the outer surface of said second arm comprising a central planar surface and a pair of opposed side surfaces extending in diverging anguular relation from opposite ends of said central planar surface towards, respectively, said pivotal connection means and said means for releaseably maintaining said arms in a closed condition;
   (h) said second arm being thinner than said firsts arm to facilitate insertion of the device around a blood vessel.

3. A disposable vascular occluder device for temporarily stopping or interrupting arterial or venous blood flow in an artery or vein during surgical procedures, comprising,
   (a) a first arm having an outer surface and an inner surface, said inner surface having a cavity therein;
   (b) a second arm having an outer surface and an inner surface, said inner surface having a cavity therein;
   (c) partially-inflated balloon means provided in said first and second arm cavities;
   (d) means pivotally connecting said first and second arms at first ends thereof, to permit said arms to be pivoted towards each other to assume a closed condition in which the inner surfaces thereof are in confronting relation, and pivoted away from each other to assume an open condition;

(e) means for releaseably maintaining said arms in said closed condition, in which said inner surfaces are in said confronting relation;

(f) whereby said arms, when in said open condition thereof, can be inserted around a blood vessel and can thereafter be pivoted to said closed condition thereof, wherein said blood vessel is occluded between said balloon means under soft pressure with minimized trauma to the blood vessel;

(g) the outer surface of said second armn comprising a central planar surface and a pair of opposed side surfaces extending in diverging angular relation from opposite ends of said central planar surface towards, respectively, said pivotal connection means and said means for releaseably maintaining said arms in a closed condition;

(h) said balloon means comprising a first partially-inflated balloon provided in said first arm cavity and a second partially-inflated balloon provided in said second arm cavity.

4. A disposable vascular occluder device according to claim 3, further comprising means for controllably inflating said first partially-inflated balloon beyond said partially-inflated state to adjust the pressure of said balloon means on said blood vessel.

5. A disposable vasculuar occluder device for temporarily stopping or interrupting arterial or venous blood flow in an artery or vein during surgical procedures, comprising, (a) a first arm having an outer surface and an inner surface, said inner surface having a cavity therein;

(b) a second arm having an outer surface and an inner surface, said inner surface having a cavity therein;

(c) partially-inflated balloon means provided in said first and second arm cavities;

(d) means pivotally connecting said first and second arms at first ends thereof, to permit said arms to be pivoted towards each other to assume a closed condition in which the inner surfaces thereof are in confronting relation, and pivoted away from each other to assume an open condition;

(e) means for releasably maintaining said arms in said closed condition, in which said inner surfaces are in said confronting relation;

(f) whereby said arms, when in said open condition thereof, can be inserted around a blood vessel and can thereafter be pivoted to said closed condition thereof, wherein said blood vessel is occluded between said balloon means under soft pressure with minimized trauma to the blood vessel;

(g) the outer surface of said second arm comprising a central planar surface and a pair of opposed side surfaces extending in diverging angular relation from opposite ends of said central planar surface towards, respectively, said pivotal connection means and said means for releasably maintaining said arms in a closed condition;

(h) said means for releaseably maintaining said arms in said closed position comprising toothed latches on second ends of said first and second arms for removably interlocking said second ends in a plurality of positions corresponding respectively to a plurality of pressure conditions;

(i) said controlled inflation means comprising a one-way valve in said first arm communicating with said first balloon, whereby said first balloon can be controllably inflated by a syringe inserted into said valve.

6. A disposable vascular occluder device for temporarily stopping or interrupting arterial or venous blood flow in an artery or vein during surgical procedures, comprising, (a) a first arm having an outer surface and an inner surface, said inner surface having a cavity therein;

(b) a second arm having an outer surface and an inner surface, said inner surface having a cavity therein;

(c) partially-inflated balloon means provided in said first and second arm cavities;

(d) means pivotally connecting said first and second arms at first ends thereof, to permit said arms to be pivoted towards each other to assume a closed condition in which the inner surfaces thereof are in confronting relation, and pivoted away from each other to assume an open condition;

(e) means for releaseably maintaining said arms in said closed condition, in which said inner surfaces are in said confronting relation;

(f) whereby said arms, when in said open condition thereof, can be inserted around a blood vessel and can thereafter be pivoted to said closed condition thereof, wherein said blood vessel is occluded between said balloon means under soft pressure with minimized trauma to the blood vessel;

(g) the outer surface of said second arm comprising a central planar surface and a pair of opposed side surfaces extending in diverging angular relation from opposite ends of said central planar surface towards, respectively, said pivotal connection means and said means for releaseably maintaining said arms in a closed condition;

(h) the inner surface of said first arm comprising a pair of opposed side surfaces extending in diverging, angular relation from opposite ends of said first arm cavity towards, respectively, said pivotal connection means and said means for releaseably maintaining said arms in a closed condition, whereby said device has a hexagonal profile.

7. A disposable vascular occluder device for temporarily stopping or interrupting arterial or venous blood flow in an artery or vein during surgical procedures, comprising, (a) a first arm having an outer surface and an inner surface, said inner surface having a cavity therein;

(b) a second arm having an outer surface and an inner surface, said inner surface having a cavity therein;

(c) partially-inflated balloon means provided in said first and second arm cavities;

(d) means pivotally connecting said first and second arms at first ends thereof, to permit said arms to be pivoted towards each other to assume a closed condition in which the inner surfaces thereof are in confronting relation, and pivoted away from each other to assume an open condition;

(e) means for releaseably maintaining said arms in said closed condition, in which said inner surfaces are in said confronting relations;

(f) whereby said arms, when in said open condition thereof, can be inserted around a blood vessel and can thereafter be pivoted to said closed condition thereof, wherein said blood vessel is occluded between said balloon means under soft pressure with minimized trauma to the blood vessel;

(g) said second arm being thinner than said first arm to facilitate insertion of the device around a blood vessel.

8. A disposable vascular occluder device for temporarily stopping or interrupting arterial or venous blood flow in an artery or vein during surgical procedures, comprising,
 (a) a first arm having an outer surface and an inner surface, said inner surface having a cavity therein;
 (b) a second arm having an outer surface and an inner surface, said inner surface having a cavity therein;
 (c) partially-inflated balloon means provided in said first and second arm cavities;
 (d) means pivotally connecting said first and second arms at first ends thereof, to permit said arms to be pivoted towards each other to assume a closed condition in which the inner surfaces thereof are in confronting relation, and pivoted away from each other to assume an open condition;
 (e) means for releaseably maintaining said arms in said closed condition, in which said inner surfaces are in said confronting relations;
 (f) whereby said arms, when in said open condition thereof, can be inserted around a blood vessel and can thereafter be pivoted to said closed condition thereof, wherein said blood vessel is occluded between said balloon means under soft pressure with minimized trauma to the blood vessel;
 (g) said balloon means comprising a first partially-inflated balloon provided in said first arm cavity and a second partially-inflated balloon provided in said second arm cavity.

* * * * *